US012502482B2

(12) United States Patent
Hee-Hanson et al.

(10) Patent No.: US 12,502,482 B2
(45) Date of Patent: Dec. 23, 2025

(54) COLLAR CAM LOCK FOR INJECTION DEVICES

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/619,754

(22) Filed: Mar. 28, 2024

(65) Prior Publication Data

US 2025/0303067 A1 Oct. 2, 2025

(51) Int. Cl.

*A61M 5/32* (2006.01)
*A61M 5/20* (2006.01)
*A61M 5/24* (2006.01)

(52) U.S. Cl.

CPC ........ *A61M 5/2033* (2013.01); *A61M 5/2466* (2013.01); *A61M 5/326* (2013.01); (Continued)

(58) Field of Classification Search

CPC ........ A61M 2005/3267; A61M 5/3271; A61M 5/3272

See application file for complete search history.

(56) References Cited

U.S. PATENT DOCUMENTS 4,900,311 A 2/1990 Stern et al.
5,088,986 A 2/1992 Nusbaum (Continued)

FOREIGN PATENT DOCUMENTS

WO WO 2011/123024 A1 10/2011
WO WO 2014/115241 A1 7/2014

(Continued)

OTHER PUBLICATIONS

Needle-based injection systems for medical use requirements and test methods, Part 1: Needle injection systems, ISO 11608-1:2014(E), Third Edition, Switzerland, ISO, Dec. 15, 2014, pp. 1-13.

(Continued)

*Primary Examiner* — Emily L Schmidt
(74) *Attorney, Agent, or Firm* — Fish & Richardson P.C.

(57) ABSTRACT

According to a first aspect of this disclosure, there is described an injection device includes: a body; a needle shroud retractable into the body including a shroud pin; a collar rotatable with respect to the body and including a cam track engageable with the shroud pin. The cam track includes: a first portion configured to, during retraction of the needle shroud into the body, guide the shroud pin from an initial position to a hold position and cause the collar to rotate relative to the body; a second portion configured to, during extension of the needle shroud from the body subsequent to the retraction, guide the shroud pin from the hold position to a final position and cause the collar to further rotate relative to the body; and a non-return surface configured to, subsequent to the extension, prevent further retraction of the needle shroud into the body.

19 Claims, 9 Drawing Sheets

(52) U.S. Cl.
CPC ..... *A61M 5/3272* (2013.01); *A61M 2005/206* (2013.01); *A61M 2005/2474* (2013.01); *A61M 2005/3247* (2013.01); *A61M 5/3271* (2013.01)

(56) References Cited

U.S. PATENT DOCUMENTS

| | | | | |
|---|---|---|---|---|
| 5,290,256 | A | 3/1994 | Weatherford et al. | |
| 5,688,241 | A | 11/1997 | Asbaghi | |
| 7,597,685 | B2 | 10/2009 | Olson | |
| 8,016,797 | B2 | 9/2011 | Gratwohl et al. | |
| 8,821,451 | B2 | 9/2014 | Daniel | |
| 9,199,038 | B2 | 12/2015 | Daniel | |
| 9,408,976 | B2 | 8/2016 | Olson et al. | |
| 9,498,579 | B2 | 11/2016 | Ruan | |
| 9,662,452 | B2 | 5/2017 | Daniel | |
| 9,867,940 | B2 | 1/2018 | Holmqvist et al. | |
| 9,919,107 | B2 | 3/2018 | Imai et al. | |
| 10,420,898 | B2 | 9/2019 | Daniel | |
| 11,369,751 | B2 | 6/2022 | Ruan et al. | |
| 11,944,787 | B2 | 4/2024 | Franke | |
| 12,274,866 | B1 | 4/2025 | Hee-Hanson et al. | |
| 12,274,871 | B1 | 4/2025 | Hee-Hanson et al. | |
| 12,274,872 | B1 | 4/2025 | Hee-Hanson et al. | |
| 12,274,875 | B1 | 4/2025 | Hee-Hanson et al. | |
| 12,427,266 | B1 | 9/2025 | Hee-Hanson et al. | |
| 2006/0276756 | A1 | 12/2006 | Francavilla | |
| 2010/0268170 | A1 | 10/2010 | Carrel et al. | |
| 2012/0203186 | A1 | 8/2012 | Vogt et al. | |
| 2013/0041328 | A1 | 2/2013 | Daniel | |
| 2013/0096512 | A1 | 4/2013 | Ekan et al. | |
| 2013/0123710 | A1 | 5/2013 | Ekman et al. | |
| 2013/0261559 | A1 | 10/2013 | Werbickas | |
| 2013/0289525 | A1 | 10/2013 | Kemp et al. | |
| 2014/0025013 | A1* | 1/2014 | Dowds | A61M 5/3272 604/198 |
| 2015/0190580 | A1 | 7/2015 | Imai et al. | |
| 2015/0258283 | A1 | 9/2015 | Imai et al. | |
| 2016/0089498 | A1 | 3/2016 | Daniel | |
| 2017/0239427 | A1 | 8/2017 | Mehawej et al. | |
| 2018/0064875 | A1 | 3/2018 | Holmqvist | |
| 2018/0104414 | A1* | 4/2018 | Karlsson | A61M 5/2033 |
| 2018/0361082 | A1 | 12/2018 | Sall et al. | |
| 2020/0179614 | A1* | 6/2020 | Mcelroy | A61M 5/3271 |
| 2020/0289755 | A1 | 9/2020 | Franke | |
| 2021/0093796 | A1 | 4/2021 | Finkelstein et al. | |
| 2021/0236732 | A1* | 8/2021 | Chu | A61M 5/3157 |
| 2021/0244887 | A1 | 8/2021 | Halseth | |
| 2021/0393886 | A1 | 12/2021 | Nicolas et al. | |
| 2022/0176042 | A1* | 6/2022 | Belisle | A61M 5/3204 |
| 2022/0387719 | A1 | 12/2022 | Wang et al. | |
| 2022/0395642 | A1* | 12/2022 | Karlsson | A61M 5/2033 |
| 2023/0338662 | A1 | 10/2023 | Böstrom | |
| 2024/0139430 | A1 | 5/2024 | Chansavang et al. | |
| 2024/0165346 | A1 | 5/2024 | Chansavang et al. | |
| 2025/0303073 | A1 | 10/2025 | Hee-Hanson et al. | |

FOREIGN PATENT DOCUMENTS

| | | | |
|---|---|---|---|
| WO | WO 2021/008839 | A1 | 1/2021 |
| WO | WO 2023/104512 | A1 | 6/2023 |
| WO | WO 2023/151957 | A1 | 8/2023 |

OTHER PUBLICATIONS

U.S. Appl. No. 18/619,991, filed Mar. 28, 2024, Alexander Hee-Hanson.
U.S. Appl. No. 18/620,210, filed Mar. 28, 2024, Alexander Hee-Hanson.
U.S. Appl. No. 18/620,586, filed Mar. 28, 2024, Alexander Hee-Hanson.
U.S. Appl. No. 18/619,996, filed Mar. 28, 2024, Alexander Hee-Hanson.
U.S. Appl. No. 18/620,097, filed Mar. 28, 2024, Alexander Hee-Hanson.
International Search Report and Written Opinion in International Appln. No. PCT/US2025/021718, mailed on May 8, 2025, 16 pages.
International Search Report and Written Opinion in International Appln. No. PCT/US2025/021774, mailed on May 8, 2025, 17 pages.
International Search Report and Written Opinion in International Appln. No. PCT/US2025/021787, mailed on May 15, 2025, 18 pages.
International Search Report and Written Opinion in International Appln. No. PCT/US2025/021782, mailed on May 30, 2025, 17 pages.
International Search Report and Written Opinion in International Appln. No. PCT/US2025/021785, mailed on Jun. 13, 2025, 18 pages.
International Search Report and Written Opinion in International Appln. No. PCT/US2025/021778, mailed on Jun. 27, 2025, 19 pages.

* cited by examiner

COLLAR CAM LOCK FOR INJECTION DEVICES

TECHNICAL FIELD

This application relates to an injector device for delivery of a medicament, e.g., to an auto-injector device.

BACKGROUND

An auto-injector may be described as a device which completely or partially replaces the activities involved in parenteral drug delivery from a standard syringe. Typically, these include removal of the protective syringe cap, insertion of the needle, injection of drug and possibly removal and shielding of the used needle. Administering an injection is a process which presents several risks and challenges, both mental and physical. The use of an auto-injector can bring many benefits for the user and healthcare professional.

Many auto-injectors have a needle cover which is biased by a spring (the needle cover spring) to extend out of the device. On removal of the device from the injection site, this spring automatically extends the needle cover past the needle to provide needle shielding. On activation of the device, the needle cover is pushed into the device. A user has to provide the force to actuate the needle cover, overcome the activation mechanism forces and compress the needle cover spring (activation force). During drug delivery the user must hold the device at the injection site and apply a force (hold force) parallel to the needle cover direction of extension to react the needle cover biasing member.

If the activation or hold force is too high or has a certain profile, it can lead to use issues such as incorrectly thinking the device is not working, inadvertent early removal or a wet injection site. Some users have difficulty applying this hold force during the full drug delivery time. This results in pain, discomfort, a wet injection site, early device removal and partial drug delivery.

SUMMARY

According to a first aspect of this disclosure, there is described an injection device including: an injection device body; a needle shroud retractable into the injection device body including a shroud pin; a collar rotatable with respect to the injection device body and including a cam track engageable with the shroud pin. The cam track includes: a first portion configured to, during retraction of the needle shroud into the injection device body, guide the shroud pin from an initial position to a hold position and cause the collar to rotate relative to the injection device body; a second portion configured to, during extension of the needle shroud from the injection device body subsequent to the retraction, guide the shroud pin from the hold position to a final position and cause the collar to further rotate relative to the injection device body; and a non-return surface configured to, subsequent to the extension, prevent further retraction of the needle shroud into the injection device body.

The first portion of the cam track may include a first angled cam track edge arranged to convert at least a portion of inward axial motion of the needle shroud into rotational motion of the collar; and the second portion of the cam track includes a second angled cam track edge arranged to convert at least a portion of outward axial motion of the needle shroud into rotational motion of the collar. The first angled cam track edge and the second angled cam track edge may partially overlap in an azimuthal direction of the collar.

The first portion and second portion of the collar may partially overlap at least at the hold position.

The non-return surface may include an angled surface or a horizontal surface arranged to trap the shroud pin when further retraction of the needle shroud into the injection device body is attempted.

The injection device may further include a control spring to bias the needle shroud towards an extended position.

The injection device may further include: a plunger including one or more recesses; a rear casing including one or more toothed beams, the one or more toothed beams each including a tooth engageable with the one or more recesses of the plunger; and biasing means for biasing the plunger in a distal direction of the injection device. The one or more recesses and/or the one or more teeth may be shaped to urge the one or more toothed beams out of the one or more recesses when the plunger is moved in the distal direction of the injection device. Each tooth may include a bevel at a proximal end of the tooth. The collar may surround at least a part of the casing that includes the one or more toothed beams. An internal surface of the collar may include one or more recesses arranged to allow the one or more toothed beams to flex outwardly when the collar is rotated, thereby to release the plunger.

The shroud pin may extend inwardly from the needle shroud in a radial direction.

The injection device may further include a needle. The needle shroud may be arranged to shroud the needle when in an extended position.

The injection device may further include a medicament cartridge containing a medicament.

According to a further aspect of this specification, there is described a collar for an injection device including a cam track engageable with a shroud pin of a needle shroud. The cam track includes: a first portion configured to, during retraction of the needle shroud into the injection device body, guide the shroud pin from an initial position to a hold position and cause the collar to rotate relative to the injection device body; a second portion configured to, during extension of the needle shroud from the injection device body subsequent to the retraction, guide the shroud pin from the hold position to a final position and cause the collar to further rotate relative to the injection device body; and a non-return surface configured to, subsequent to the extension, prevent further retraction of the needle shroud into the injection device body.

The first portion of the cam track may include a first angled cam track edge arranged to convert at least a portion of inward axial motion of the needle shroud into rotational motion of the collar. The second portion of the cam track may include a second angled cam track edge arranged to convert at least a portion of outward axial motion of the needle shroud into rotational motion of the collar. The first angled cam track edge and the second angled cam track edge may partially overlap in an azimuthal direction of the collar.

The first portion and second portion of the collar may partially overlap at least at the hold position. The non-return surface may include an angled surface or horizontal surface arranged to trap the shroud pin when further retraction of the needle shroud into the injection device body is attempted. An internal surface of the collar may include one or more recesses.

According to a further aspect of this specification, there is described a method for securing a needle shroud of an injection device after use, the method including: during retraction of the needle shroud into an injection device body, guiding a shroud pin of the needle shroud from an initial position to a hold position using a first portion of a cam track of an injection device collar, the guiding causing the injection device collar to rotate relative to the injection device body; during extension of the needle shroud from the injection device body subsequent to the retraction, guiding the shroud pin from the hold position to a final position using a second portion of the cam track of the injection device collar, the guiding causing the injection device collar to rotate relative to the injection device body; and subsequent to the extension of the needle shroud, preventing further retraction of the needle shroud into the injection device body using a non-return surface.

The first portion of the cam track may include a first angled cam track edge arranged to convert at least a portion of inward axial motion of the needle shroud into rotational motion of the collar. The second portion of the cam track includes a second angled cam track edge arranged to convert at least a portion of outward axial motion of the needle shroud into rotational motion of the collar. The first angled cam track edge and the second angled cam track edge may partially overlap in an azimuthal direction of the collar.

The first portion and second portion of the collar may partially overlap at least at the hold position. The non-return surface may include an angled surface or horizontal surface arranged to trap the shroud pin when further retraction of the needle shroud into the injection device body is attempted.

The method may further include: biasing a plunger of the injection device in a distal direction of the injection device using a biasing force; converting a portion of the biasing force into an outward force on one or more toothed beams of a casing using one or more recesses on the plunger; retaining the one or more toothed beams in an engaged position with the one or more recesses on the plunger during at least a portion of the retraction of the needle shroud into the injection device; and allowing the one or more toothed beams to flex outwardly at the hold position, thereby releasing the plunger.

Each tooth may include a bevel at a proximal end of the tooth. The collar may surround at least a part of the casing that includes the one or more toothed beams. An internal surface of the collar may include one or more recesses arranged to allow the one or more toothed beams to flex outwardly when the collar is at the hold position.

The method may further include expelling medicament from a medicament cartridge of the injection device.

Throughout this specification, use of the injection device is described in terms of a user, who operates the injection device, and a subject, who receives an injection from the injection device. The user and the subject may be the same person. Alternatively, the user and subject may be different entities, e.g., a healthcare provider and a patient.

BRIEF DESCRIPTION OF THE FIGURES

Exemplary embodiments of the present disclosure are described with reference to the accompanying drawings, in which.

DETAILED DESCRIPTION

Figure 1:
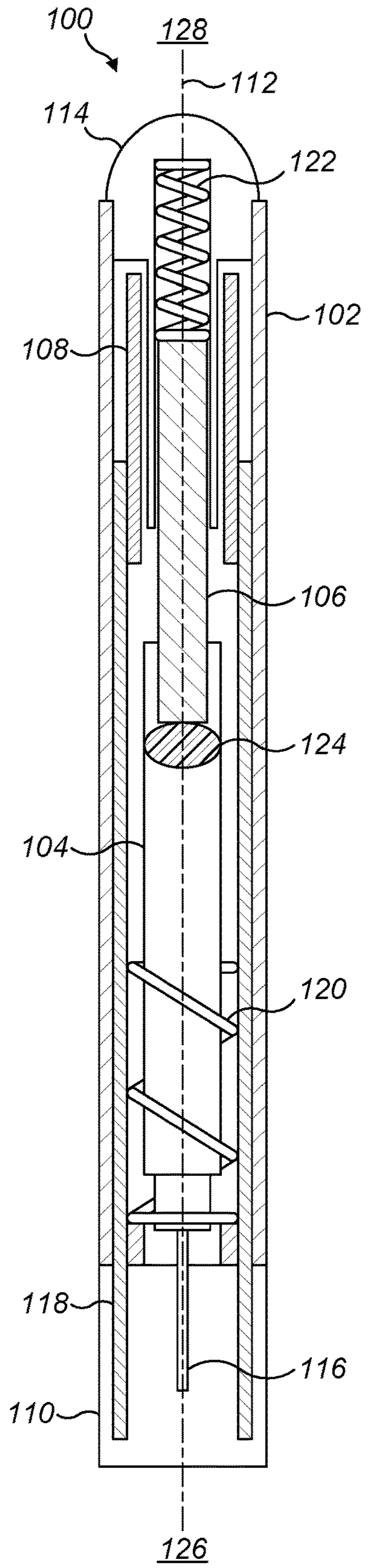
FIG. 1 shows a schematic example of a cross section of an injection device.

A drug delivery device, as described herein, may be configured to inject a medicament into a subject. For example, delivery could be sub-cutaneous, intra-muscular, or intravenous. Such a device could be operated by a subject or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a subject's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Auto-injectors require user actions to commence drug delivery. One of these actions apply an axial force to the device by either pushing a Needle Cover into the device or pressing a button on the device. The axial force required is referred to as the activation force in this document. The magnitude and profile of this activation force has an impact on the usability of the device.

After the device is removed from the user's body post use, many autoinjectors cover the needle with a shroud/needle cover, which is extended out of the device by a control spring. This shroud is locked in its extended position by a needle cover locking mechanism, often featuring a one-way clip feature. The control spring must have enough force to ensure this mechanism is activated following device removal. The user must react the control spring force during activation and hold. It may be beneficial to reduce the hold and/or activation force. Reducing the force to active the needle cover locking mechanism, enables a reduction in the control spring and therefore reduces the hold and activation forces.

Injection devices described herein use a collar cam lock as a lower force alternative to existing needle cover locking mechanisms. The injection device described herein include a rotary collar with a cam track and a pin on the shroud/needle cover that interfaces with the cam track. The collar can rotate within the injection device. The cam track converts at least a portion of the axial movement of the shroud into/out of the injection device body into a rotation of the collar. The cam track is designed so that it is self-locking. If the shroud is pushed back into the injection device body after use, the shroud pin contacts a non-return surface on the cam track, which prevents shroud movement.

The force used to rotate a collar is less than the force required to depress a locking clip as found on many auto-injector needle cover mechanisms, resulting in a reduction in required control spring force.

FIG. 1 shows a schematic example of a cross section of an injection device 100. The injection device is configured to inject a medicament into a subject's body. The injection device 100 includes an outer casing 102 that encloses a reservoir 104, a plunger 106 and a rotatable collar 108. The reservoir 104 typically contains the medicament to be injected, and may, for example, be in the form of a syringe. The injection device 100 can also include a cap assembly 110 that can be detachably mounted to the outer casing 102. Typically a user must remove cap 110 from the outer casing 102 before device 100 can be operated.

As shown, casing 102 is substantially cylindrical and has a substantially constant diameter along the longitudinal axis of the device 100. The injection device 100 has a distal region and a proximal region. The term "distal" refers to a location that is relatively closer to a site of injection, and the term "proximal" refers to a location that is relatively further away from the injection site.

The outer casing 102 is closed at a proximal end by a rear casing 114. A needle 116 and a retractable needle shroud 118 (also referred to as a "needle sleeve" or "needle cover") extend from a distal end of the outer casing 102. The retractable needle shroud 118 is biased in the distal direction of the injection device 100, for example using a control spring 120. The needle shroud 118 is coupled to the outer casing 102 to permit movement of needle shroud 118 relative to the outer casing 102. For example, the shroud 118 can move in a longitudinal direction parallel to longitudinal axis 112. Specifically, movement of shroud 118 in a proximal direction can permit a needle 116 to extend from distal region of the casing 102.

The plunger 106 is biased towards the distal end of the injection device 100 by a biasing means, for example using a drive spring 122. The plunger 106 is retained in an initial position by a combination of the rear casing 114 and the collar 108, preventing the biasing means from displacing the plunger in the distal direction. An example of such a retention mechanism is described in relation to FIG. 4. Activation of the injection device 100 causes the collar 108 to rotate, which releases the plunger 106. Once released, the biasing means causes the plunger 106 to move in the distal direction (i.e., towards the needle 116 end of the injection device 100). The plunger 106 contacts a stopper 124 in the reservoir 104, displacing the stopper 124 in the distal direction and causing medicament stored in the reservoir 104 to be expelled from the injection device 100 via the needle 116.

Activation of the injection device 100 can occur via several mechanisms. For example, the needle 116 may be fixedly located relative to the casing 102 and initially be located within an extended needle shroud 118. Proximal movement of shroud 118 by placing a distal end of the shroud 118 against a subject's body and moving casing 102 in a distal direction will uncover the distal end of the needle 116. Such relative movement allows the distal end of the needle 116 to extend into the subject's body. Such insertion is termed "manual" insertion as the needle 118 is manually inserted via the subject's manual movement of the casing 102 relative to shroud 118. Retraction of the shroud 118 into the casing 102 causes the collar 108 to rotate, releasing the plunger 106.

Another form of activation is "automated," whereby the needle 116 moves relative to casing 102. Such insertion can be triggered by movement of the shroud 118 and/or by another form of activation, such as, for example, a button (not shown).

Typically, the user presses the needle shroud 118 against an injection site to push the needle shroud 118 at least partially into the device body. The exposed needle 116 is pushed into the injection site. In a holding position, medicament is automatically dispensed from the needle 116 via an automated mechanism. A user must typically hold the needle shroud 118 in the holding position for a predetermined period of time, to ensure that the correct dose of medicament is dispensed from the device 100, before removing the device from the injection site.

The spring force from the control spring 120 against which the user must apply a force to move the needle shroud 118 is one component of an "activation force" of the device 100. The activation force refers to the force or force profile that the user must exert on the device 100 to move the needle shroud 118 from the extended position shown in FIG. 1 to a retracted position. If this force or force profile is not well balanced, it can lead to difficulty in activating the device 100 for some users, or increase the pain or anxiety associated with using the device.

Following injection, the needle 116 can be retracted within the shroud 118. Retraction can occur when the shroud 118 moves distally under the biasing of the control spring 120 as a user removes the device 100 from a subject's body. Once a distal end of shroud 118 has moved past a distal end of the needle 116, and the needle 116 is covered, and the shroud 118 is locked. Such locking can include locking any (substantial) proximal movement of the shroud 118 relative to the casing 102, i.e., preventing any movement of the shroud 118 that would uncover the needle.

Figure 2:
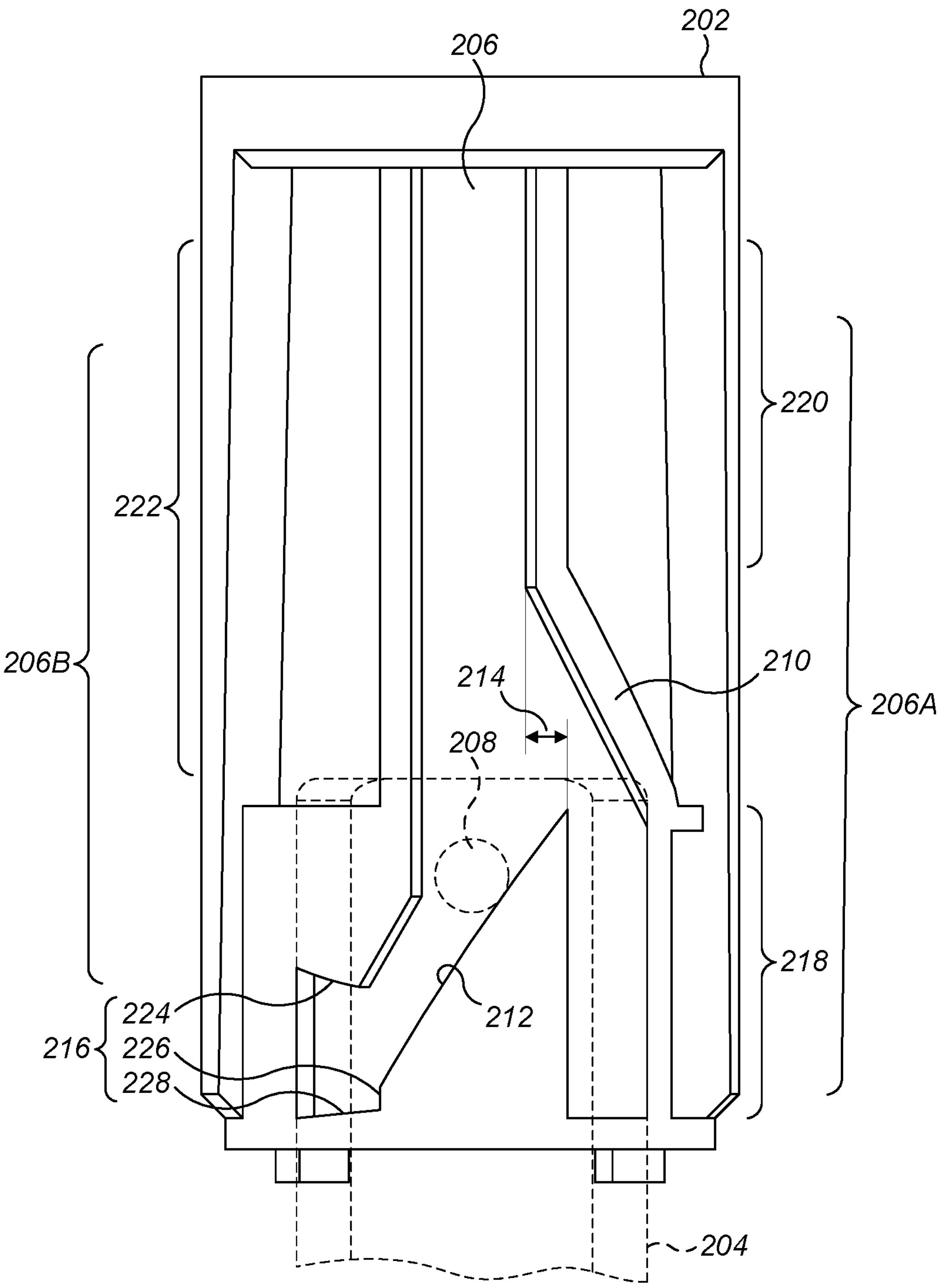
FIG. 2 shows an example of collar and needle shroud for an injection device.

FIG. 2 shows an example of collar 202 and needle shroud 204 for an injection device, e.g., the injection device of FIG. 1. The collar 202 may be a cylindrical collar that surrounds at least a part of the injection device, e.g., a casing, such as a rear casing, of the injection device. The collar includes a cam track 206 on its outer surface that engages with a shroud pin 208 of the needle shroud 204. The shroud pin 208 may extend inwards from the needle shroud 204 in the radial direction.

The cam track 206 is configured to cooperate with the shroud pin to guide the shroud pin 208 from an initial position to a hold position during retraction of the needle shroud 204 into the injection device, i.e., when the user is pressing the device against a subject's skin. During this retraction, the cam track 206 causes the collar to rotate relative to the injection device body (i.e., to the casing). In the example shown, the collar 202 is configured to rotate from left to right, e.g., anticlockwise when viewed from above. The cam track 206 is further configured to cooperate with the shroud pin to guide the shroud pin 208 from the hold position to a final (locked) position during extension of the needle shroud 204 out of the injection device after use, i.e., when the user is removing the device from a subject's skin. The cam track 206 is further configured to prevent further retraction of the shroud 204 after the shroud pin has reached the final position, i.e., after the device is removed from the subject's body, using a non-return surface 216.

In the example shown, the cam track 206 includes a first portion 206A that causes the collar to rotate by a first angle during retraction of the needle shroud 204 into the casing. The first portion 206A may include an initial cam track portion 218 that is aligned with the longitudinal axis of the injection device, i.e., parallel with longitudinal axis of the injection device. The first portion 206A further includes a first angled portion 210 of the cam track 206 including a first angled cam track edge (also referred to herein as a "ramp"). The angled portion is angled with respect to the longitudinal axis of the injection device such that the shroud pin 208 applies a force to the collar 202 during at least a portion of the retraction of the needle shroud 204 into the casing, causing the collar 202 to rotate. The first portion 206A may further include a final portion 220 that is aligned with the longitudinal axis of the injection device, i.e., parallel with longitudinal axis of the injection device.

In the example shown, the cam track 206 includes a second portion 206B that causes the collar to rotate by a second angle during extension of the needle shroud 204 from the casing. The second portion 206B may include an initial cam track portion 222 that is aligned with the longitudinal axis of the injection device, and which at least partially overlaps with the final portion 220 of the first portion 206A of the cam track. The second portion 206B further includes a second angled portion 212 of the cam track 206 including a second angled cam track edge. The angled portion is angled with respect to the longitudinal axis of the injection device such that the shroud pin 208 applies a force to the collar 202 during at least a portion of the extension of the needle shroud 204 out of the casing after it has been retracted, causing the collar 202 to rotate.

The end of the first angled cam track edge and the start of the second angled cam track edge partially overlap 214 in the azimuthal direction of the collar (i.e., in the circumferential direction). This prevents the shroud pin 208 being guided back along the first angled portion during retraction of the needle shroud 204 after the injection has occurred.

The non-return portion 216 is shaped to prevent retraction of the needle sleeve beyond the needle after the needle sleeve has extended from a hold position, i.e., after an injection has occurred and the device has been removed from a subject's body. In the example shown, the non-return portion 216 includes an angled edge 224 (also referred to as a "proximal edge") of the cam track located at a proximal portion of the non-return portion 216. The angle edge 224 is angled to apply a rotation force to the collar 202 in the same direction as the first angled portion and second angled portion when contacted by the shroud pin 208 during a further attempt to retract the needle shroud 204. This effectively traps the shroud pin 208 in the non-return portion 216, preventing further retraction of the needle shroud 204.

The non-return portion 216 may further include a vertical edge 226 linking the end of the second angled portion to a distal edge 228 of the non-return portion 216. The vertical edge 226 acts to prevent the shroud pin 208 re-entering the second angled portion, which could allow the collar 202 to rotate and the needle shroud 204 to retract again. The distal edge 228 of the non-return portion 216 may be angled to apply a rotational force to the collar in the same direction as the first angled portion and second angled portion when pushed against by the shroud pin 208, e.g., under the force of the control spring. A second vertical edge of the non-return portion links the lowest part of the distal edge 228 to the highest part of the angled edge 224.

FIGS. 3A-E shows an example of the operation of a collar and needle shroud of an injections device. The collar 302 and needle shroud 304 correspond to the collar 202 and needle shroud 204 of FIG. 2.

Figure 3B:
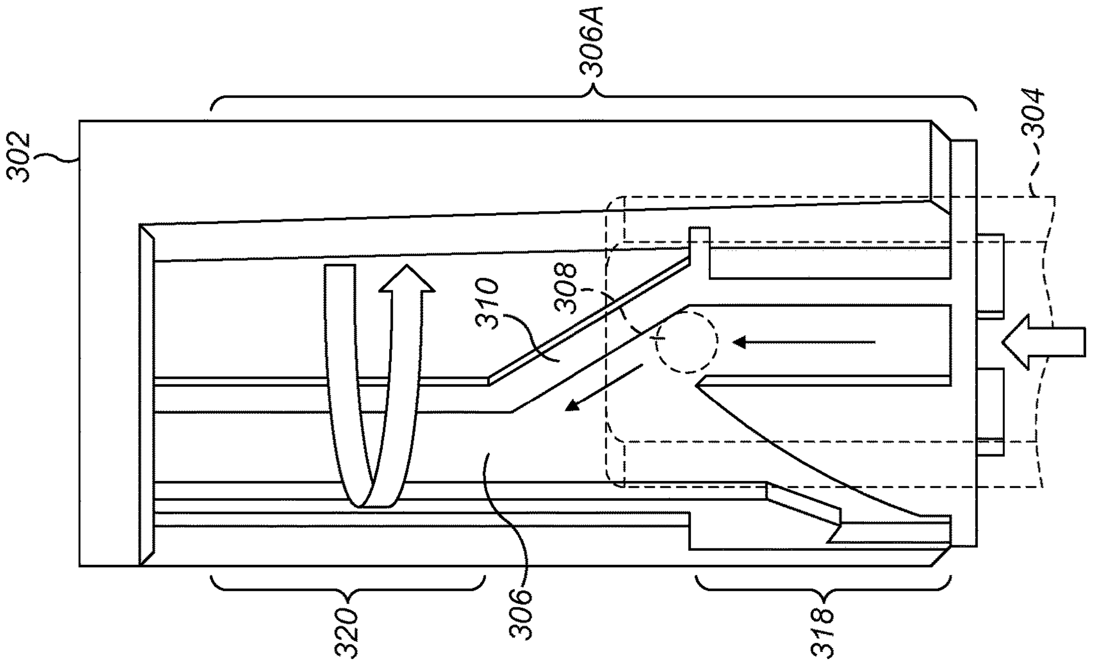
FIG. 3B shows an example of the needle shroud retracting into the injection device body.
Figure 3A:
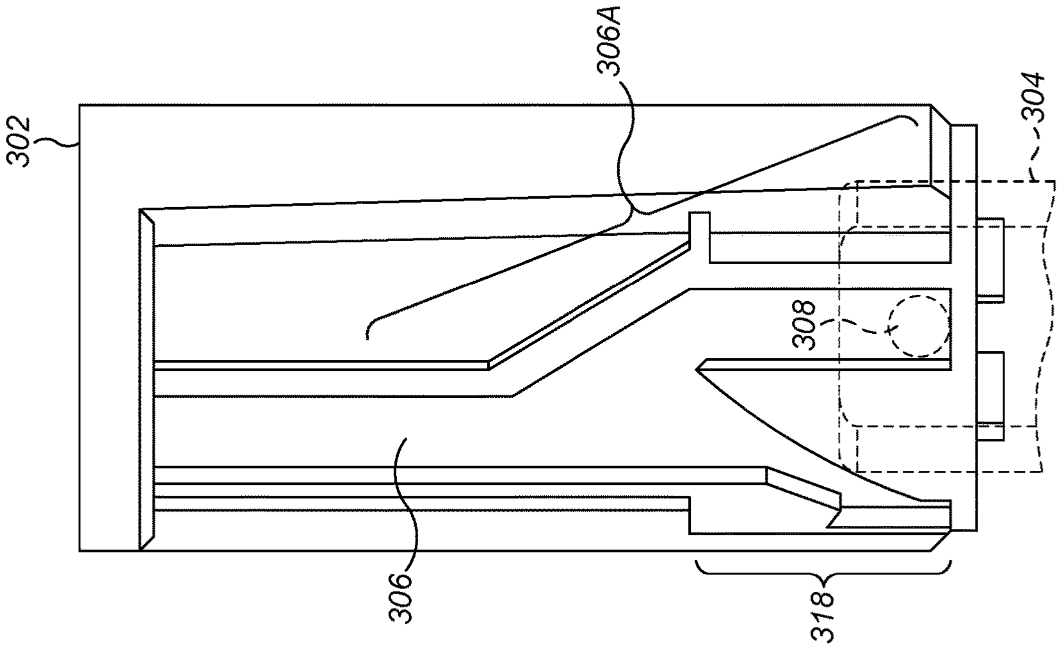
FIG. 3A shows an example of an initial configuration of the collar and needle shroud prior to retraction of the needle shroud into the injection device body.

FIG. 3A shows an example of an initial configuration of the collar 302 and needle shroud 304 prior to retraction of the needle shroud 304 into the injection device body, e.g., a pre-use position. The needle shroud 304 is in an extended position and covers a needle of the injection device. The shroud pin 308 of the needle shroud 304 is in an initial position in the cam track 306 of the collar 302. The initial position 310 lies in the initial portion 318 of the first portion 306A of the cam track 306. The shroud pin 308 is held in the initial position under a retaining force from the control spring (not shown). In this configuration the collar 302 may, in some examples, cause the plunger of the device (not shown) to be retained in an initial position, as described in relation to FIGS. 3A and 3B.

FIG. 3B shows an example of the needle shroud 304 retracting into the injection device body, e.g., during activation of the injection device when a user is pressing the needles shroud against the flesh around an injection site of a subject. As the needle shroud 304 is retracted into the injection device body, the shroud pin 308 moves along the initial part 318 of the first portion 306A of the cam track 306 in an axial direction until it reaches the first angled portion 310 of the cam track 306. Further retraction of the needle shroud 304 causes the shroud pin 308 to apply a force to the first angled portion 310 of the cam track 306, which in turn causes the collar 302 to rotate. The shroud pin 308 causes the collar 302 to rotate until the shroud pin reaches an upper end of the angled portion 310, after which further retraction of the shroud 304 causes the shroud pin 308 to move into the final portion 320 of the first portion 306A of the cam track 306 and reach a holding position.

Figure 3D:
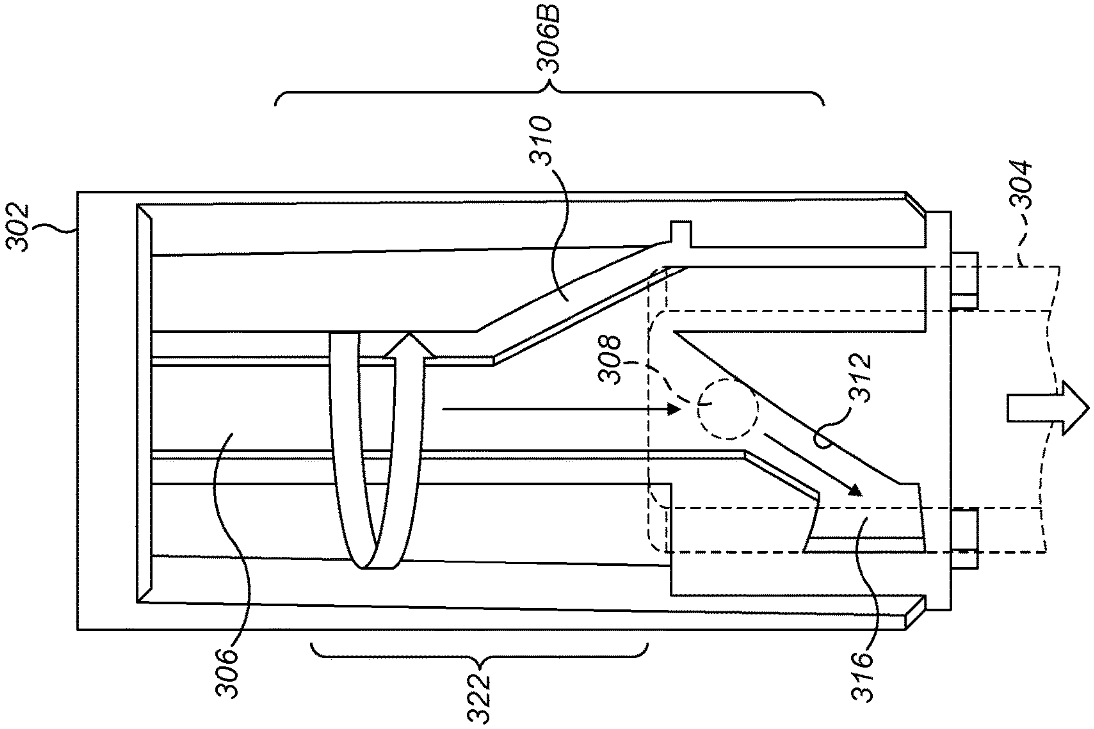
FIG. 3D shows an example of the collar moving as the needle shroud extends out of the injection device body.
Figure 3C:
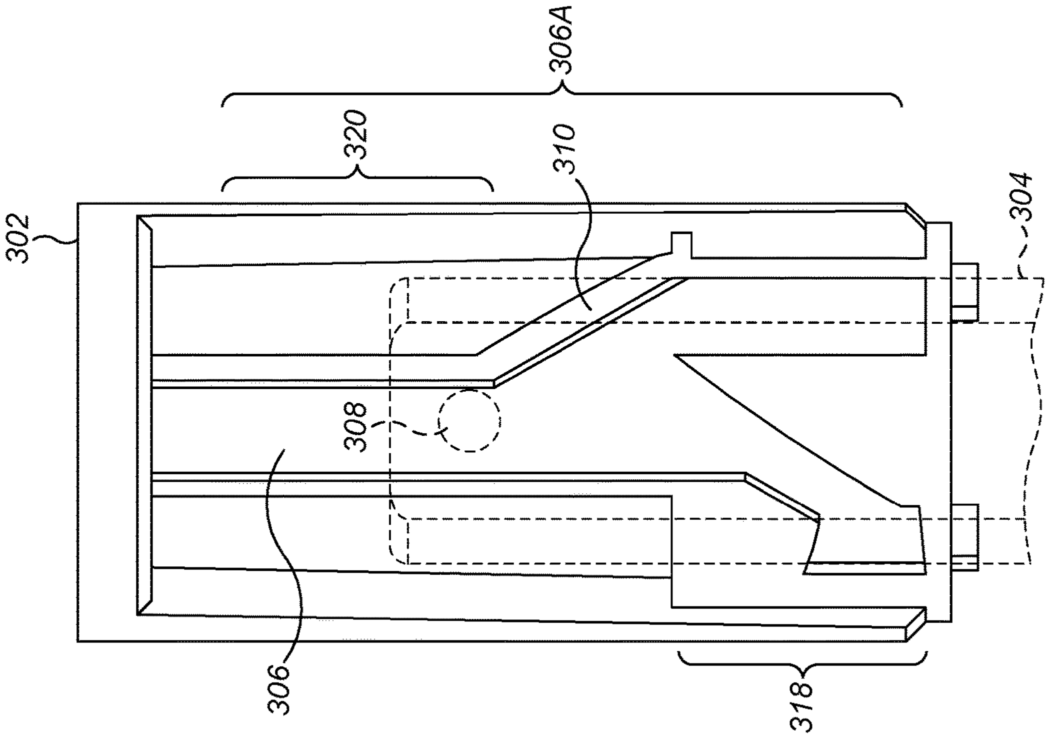
FIG. 3C shows an example of a hold configuration of the collar and needle shroud.

FIG. 3C shows an example of a hold configuration of the collar 302 and needle shroud 304, e.g., the configuration where medicament is being expelled from the injection device via a needle. In a hold position, the shroud pin 308 is held at a position in the final part 320 of the first portion of the cam track 306A by the force of the user pressing the needle shroud into the flesh around an injection site of a subject.

FIG. 3D shows an example of the collar 402 moving as the needle shroud 304 extends out of the injection device body, e.g., during removal of the needle from the body of a subject after an injection has occurred. As the needle shroud 304 extends out of the injection device, for example under the force of the control spring, the shroud pin moves along the initial part 322 of the second portion 306B of the cam track 306 until it comes into contact with the angled edge of the second angled portion 312. The overlap of the top of the second angled portion 312 and the top of the first angled portion 310 in the azimuthal direction prevents the shroud pin from returning along the first portion 306A of the cam track 306. Further extension of the needle shroud 304 causes the shroud pin 308 to apply a force to the angled edge of the second angled portion 312, causing the collar 302 to rotate. The shroud pin 308 moves along the angled edge of the second angled portion 312 until it reaches a non-return surface 316.

Figure 3E:
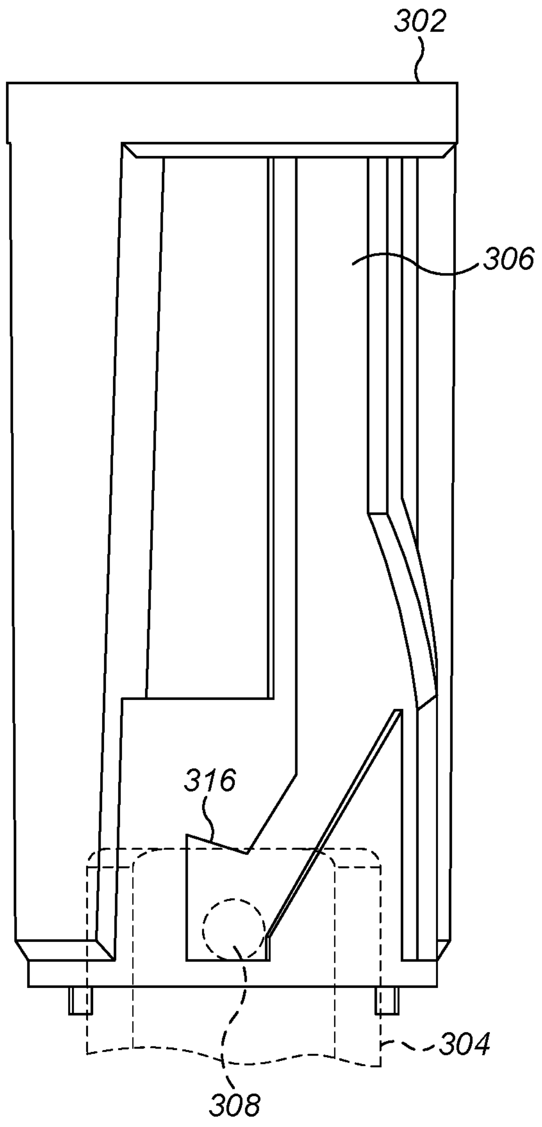
FIG. 3E shows an example of a locked configuration of the collar and needle shroud.

FIG. 3E shows an example of a locked configuration of the collar 302 and needle shroud 304, e.g., the configuration after the needle shroud 304 has extended from the device body after retraction. In this configuration, the shroud pin 308 is locked in a final portion of the cam tack 306. A non-return surface 316 prevents further retraction of the needle shroud 304 into the injection device (and thus expose of the needle) by trapping the shroud pin 308 when it moves in the axial direction.

The non-return surface 316 may, for example, include an angled surface arranged to urge the shroud pin 308 away from the second angled portion 312 when the shroud pin 308 is pushed against it during further retraction of the needle shroud 304. The start of the non-return surface (e.g., the start of the angled surface) is, in the example shown, to the right of the centre line of the shroud pin 308 in the post use position, ensuring that if the needle shroud 304 is pushed back into the device, the shroud pin 308 always contacts this surface. In examples where the collar is configured to rotate in the opposite direction to the example shown, the start of the non-return surface may be to the left of the centre line of the shroud pin 308 in the post use position. The non-return surface 316 may, in some examples, be shaped to further rotate the collar, preventing the shroud pin 308 moving back up the second angled portion 312 and returning to the initial shroud pin location.

In some examples (not shown), the non-return surface 316 could be a horizontal surface (i.e., arranged along the azimuthal direction) configured to trap the shroud pin 308. In such examples, any force from the shroud pin 308 is not converted into a rotation, and instead the shroud pin 308 is trapped.

FIGS. 4A-D show examples of a plunger release mechanism cooperating with a collar of an injection device.

Figure 4B:
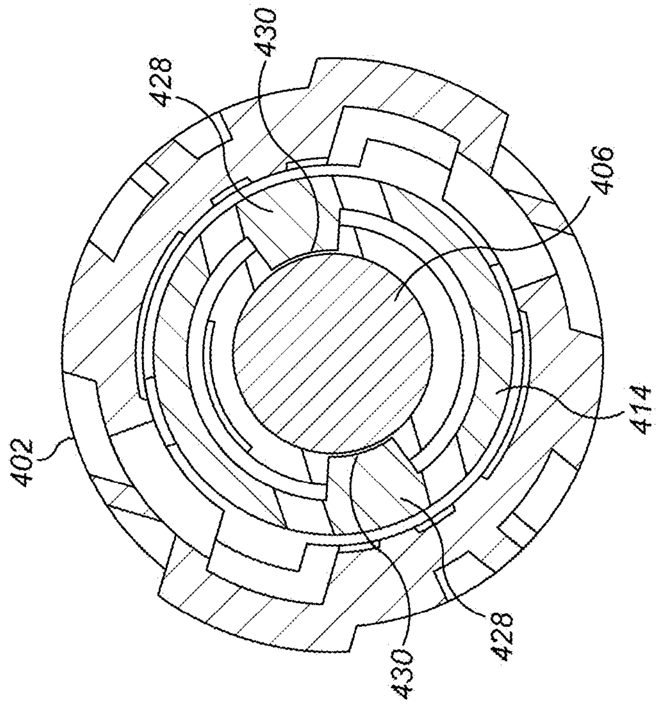
FIG. 4B shows an example of a cross section of an injection device in a plane through the teeth of the toothed beams prior to release of the plunger.
Figure 4A:
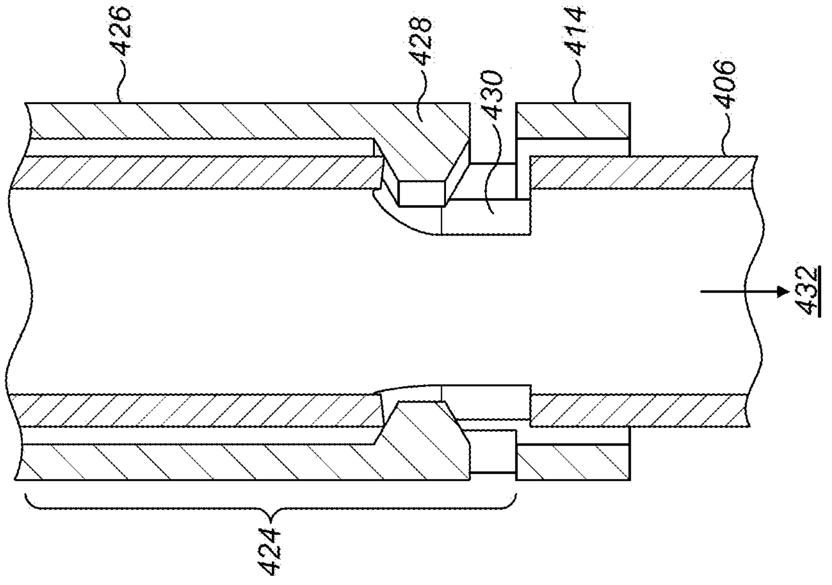
FIG. 4A shows a cut-away view of an example of a plunger and a rear casing.

FIG. 4A shows a cut-away view of an example of a plunger 406 and a rear casing 414. The rear casing 414 includes one or more (e.g., two or three) toothed beams 424. Each toothed beam includes a flexible arm 426 and a tooth 428. The plunger 406 includes a corresponding one or more recesses 430 which can each engage with a tooth 428 of the toothed beams 424. In some examples, the recesses 430 and toothed beams 424 are evenly spaced around the plunger 406 and rear casing 414 respectively, e.g., spaced at 180 degrees around the plunger 406 and rear casing 414 for two recesses and teeth, spaced at 120 degrees around the plunger 406 and rear casing 414 for three recesses and teeth, etc. While held in the recesses 430 (e.g., by the collar, as described in relation to FIG. 4B), the teeth 428 of the toothed beams 424 prevent the plunger 406 from moving in the distal direction 432.

The one or more recesses 430 and/or corresponding teeth 428 are shaped to urge the toothed beams 424 outwards when a force is applied to the plunger 406 in the distal direction 432. For example, each tooth 428 may include a bevel (e.g., be chamfered) at its proximal end (and may, in some examples also be bevelled at its distal end). When the plunger 406 moves/is urged in the distal direction 432 (e.g., under the force of a driving spring), an upper (i.e., proximal portion) of each recess 430 contacts the bevel of its respective tooth 428 and applies an outward force to the respective toothed beam 424. In the absence of retention, e.g., by a collar, this causes the toothed beams 424 to flex outwards, releasing the plunger 406 and allowing an injection to proceed.

FIG. 4B shows an example of a cross section of an injection device in a plane through the teeth 428 of the toothed beams prior to release of the plunger 406. The portion of the rear casing 414 including the toothed beams is surrounded by the collar 402 of the injection device, which prevents the teeth 428 of the toothed beams from flexing outwards due to the force applied on them by the recess 430 of the plunger 406.

Figure 4C:
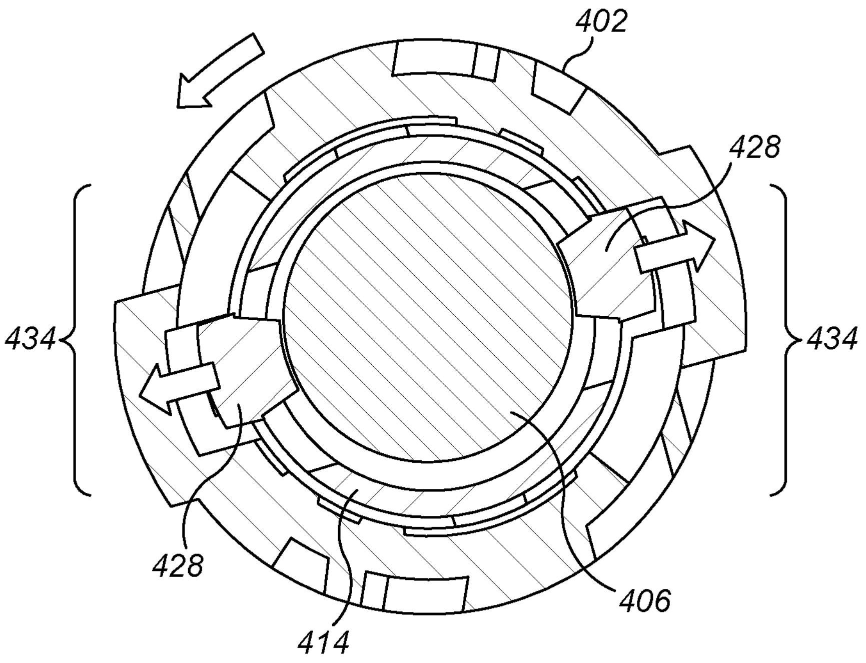
FIG. 4C shows an example of a cross section of an injection device in a plane through the teeth of the toothed beams during release of the plunger.

FIG. 4C shows an example of a cross section of an injection device in a plane through the teeth 428 of the toothed beams during release of the plunger 406. As the collar 402 rotates during retraction of the needle shroud into the injection device, one or more recesses 434 in the inner surface of the collar 402 rotates over the teeth 428 of the toothed beams. This provides space for the toothed beams to be forced outwards in a radial direction by their respective plunger recesses 430, thereby releasing the plunger 406. The one or more recesses 434 may be arranged to allow release of the plunger 406 when the shroud pin of the needles shroud enters the final part of the first portion of the cam track (i.e., feature 220 in FIG. 2 and feature 320 in FIGS. 3A-3C).

Figure 4D:
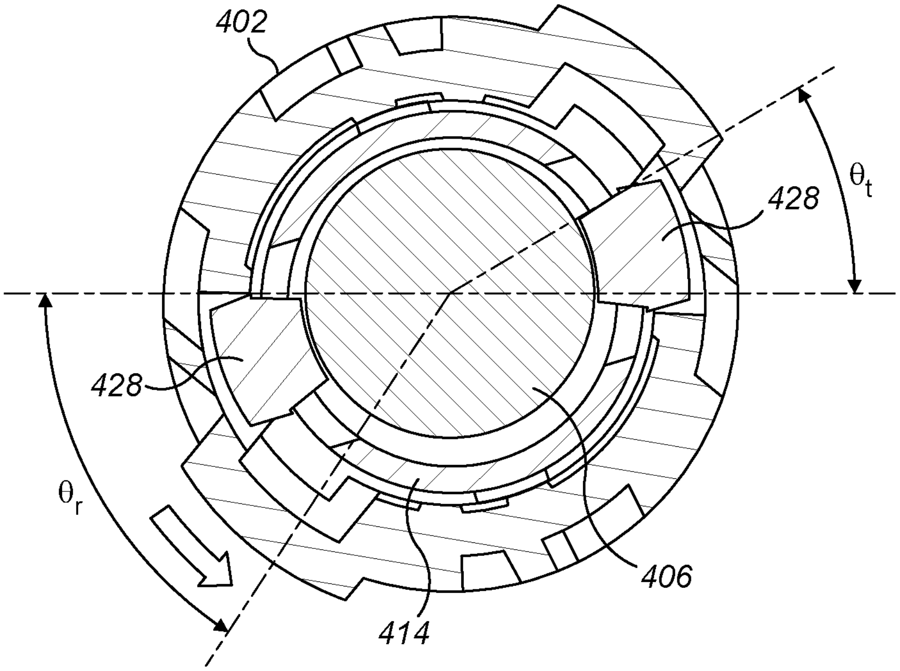
FIG. 4D shows an example of a cross section of an injection device in a plane through the teeth of the toothed beams after an injection is completed.

FIG. 4D shows an example of a cross section of an injection device in a plane through the teeth 428 of the toothed beams after an injection is completed. The one or more recesses 434 have an angular size, $\theta_r$, greater than the angular size, $\theta_t$, of the teeth 428, allowing further rotation of the collar with respect to the plunger 406 and rear casing 414 after the release of the plunger 406. For example, the angular size of a recess, $\theta_r$, is at least enough to allow the rotation of the collar 402 caused by the extension of the needle shroud out the injection device until the shroud pin reaches the non-return surface.

Figure 5:
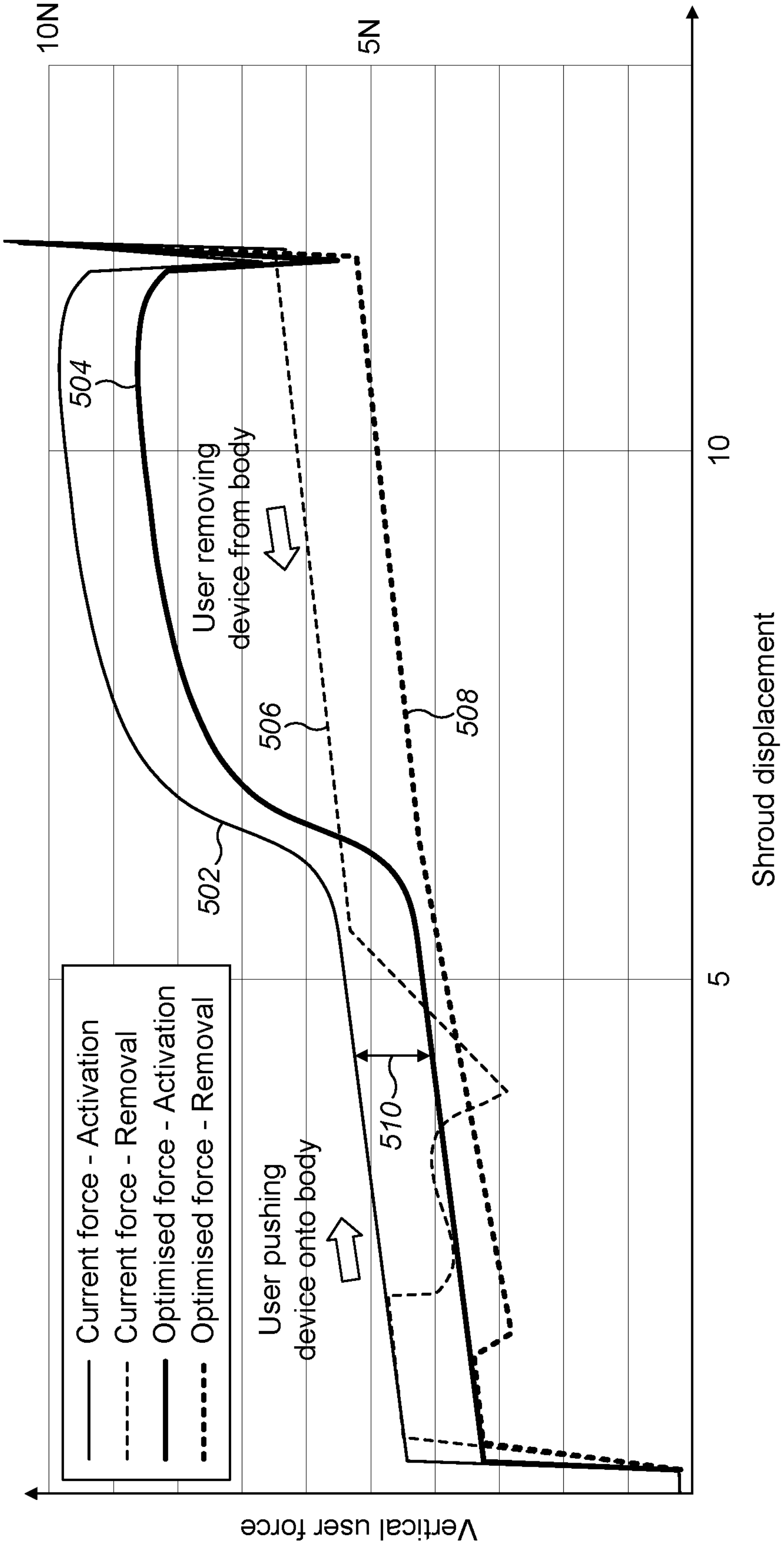
FIG. 5 shows an example comparison of force profiles of an injection device during use.

FIG. 5 shows an example comparison of force profiles of an injection device during use. The graph shows a vertical force applied (in Newtons, N) by a user as a function of needle shroud displacement (in mm) during insertion and removal of the device from a subject's body for both a prior art injection device (e.g., using a prior art needle locking mechanism) and a device using a collar as described herein.

The first trace 502 shows the force profile of the activation force of a prior art device when a user is pushing the device onto a subject's body. The second trace 504 shows the force profile of the activation force of an injection device 100 according to embodiments of the present disclosure, when the user is pushing the device onto a subject's body. The third trace 506 shows the force profile of a prior art device when a user is removing the device 110 from a subject's body. The fourth trace 508 shows the force profile of an injection device 100 according to embodiments of the present disclosure, when the user is removing the device from a subject's body.

The double headed arrow 510 shows a reduction in the activation force for the device 100 when using embodiments of the present disclosure. Since the control spring does not need to overcome/activate a locking mechanism, such as a one-way clip, the force applied by the control spring to the needle shroud can be reduced. This reduced the force that a user has to apply to cause the needle shroud to retract into the device and for holding the device in position during the injection (the hold force). In the example shown, the activation force and hold force are reduced by approximately 1 N.

The removal force profile for the device utilising embodiments described herein differs from the prior art device in that the force profile is generally smoother than the prior art force profile, since the prior art force profile has to engage and activate a one-way clip. By contrast, the device utilising embodiments described herein only engages the cam track, which causes the collar to rotate.

Figure 6:
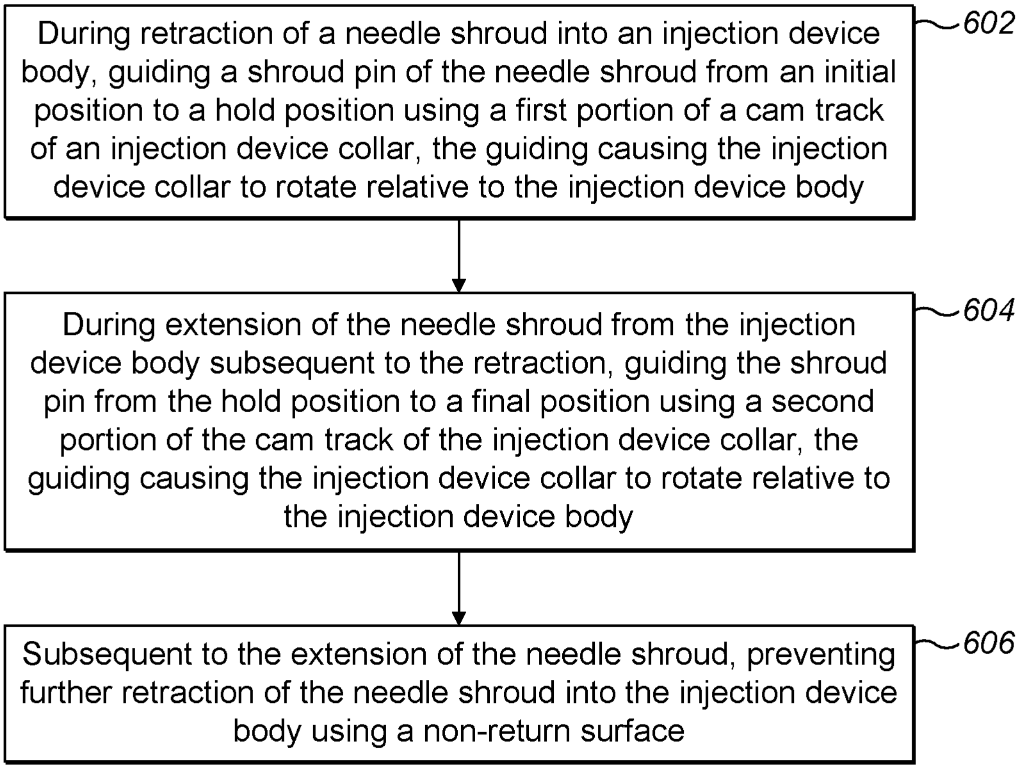
FIG. 6 shows a flow diagram of an example method of securing a needle shroud of an injection device.

FIG. 6 shows a flow diagram of an example method of securing a needle shroud of an injection device. The method corresponds to the operations described in relation to FIGS. 3A-E.

At operation 602, during retraction of a needle shroud into an injection device body, a shroud pin of the needle shroud is guided from an initial position to a hold position using a first portion of a cam track of an injection device collar.

The first portion of the cam track includes a first angled portion between the initial position and the hold position that is angled to cause rotation of the collar when the shroud pin is urged against it. The first portion of the cam track may further include an initial portion that is parallel to a longitudinal axis of the injection device, and that extends from the initial position to a start of the first angled portion. The first portion of the cam track may further include a final part that is parallel to a longitudinal axis of the injection device, and that extends from the end of the first angled portion. The hold position may lie in the final part of the first portion of the cam track.

In some examples, the method further includes causing release of a plunger of the injection device when the shroud pin reaches the final part of the first portion of the cam track. For example, when the collar rotation is such that the shroud pin enters the final part of the first portion of the cam track, one or more recesses in an inner surface of the collar may align with respective teeth on a rear casing of the injection device, allowing them to be urged outwards by respective recesses on the plunger.

At operation 604, during extension of the needle shroud from the injection device body subsequent to the retraction, the shroud pin is guided from the hold position to a final position using a second portion of the cam track of the injection device collar, the guiding causing the injection device collar to rotate relative to the injection device body. The rotation is in the same direction (e.g., clockwise or anticlockwise) as the rotation caused by the first portion of a cam track during retraction of the needle shroud.

The second portion of the cam track includes a second angled portion between the hold position and the final position that is angled to cause rotation of the collar when the shroud pin is urged against it. The second portion of the cam track may further include an initial portion that is parallel to a longitudinal axis of the injection device, and that includes the hold position and extends to a start of the second angled portion. The initial portion of the second portion of the cam track at least partially overlaps with the final part of the first portion of the cam track.

At operation 606, subsequent to the extension of the needle shroud, further retraction of the needle shroud into the injection device body is prevented using a non-return surface. The non-return surface may include an angled edge that urges the collar in the same rotation direction as the first and second angled portions, i.e., prevents the collar rotating back to the hold or initial positions.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms “analogue” and “derivative” refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as “insulin receptor ligands”. In particular, the term “derivative” refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091 MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term “antibody”, as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS

100—injection device
102—outer casing/housing
104—reservoir
106—plunger
108—collar
110—cap
112—longitudinal axis
114—rear casing
116—needle
118—needle shroud/sleeve/cover
120—control spring
122—drive spring
124—stopper
126—distal end
128—proximal end
202—collar
204—needle shroud/sleeve/cover
206—cam track
206A—first portion of cam track
206B—second portion of cam track
208—shroud pin
210—first angled portion
212—second angled portion
214—overlap
216—non-return surface/portion
218—initial part of first portion of the cam track
220—final part of first portion of the cam track
222—initial part of second portion of the cam track
224—angled edge of the non-return portion
226—vertical edge of the non-return portion
228—distal edge of the non-return portion
302—collar
304—needle shroud/sleeve/cover
306—cam track

306A—first portion of cam track
306B—second portion of cam track
308—shroud pin
310—first angled portion
3312—second angled portion
316—non-return surface
318—initial part of first portion of the cam track
320—final part of first portion of the cam track
322—initial part of second portion of the cam track
402—collar
406—plunger
414—rear casing
424—toothed arm
426—flexible arm
428—tooth
430—recess in plunger
434—recess in collar
502—Force profile of prior art device during insertion
504—Force profile of embodiments during insertion
502—Force profile of prior art device during removal
504—Force profile of embodiments during removal

The invention claimed is:

1. An injection device comprising:

an injection device body;

a needle shroud retractable into the injection device body and comprising a shroud pin;

a collar rotatable with respect to the injection device body and comprising a cam track engageable with the shroud pin;

a plunger comprising one or more recesses;

one or more toothed beams, the one or more toothed beams comprising one or more teeth engageable with the one or more recesses of the plunger, wherein the collar surrounds at least a part of a rear casing that comprises the one or more toothed beams; and a resilient member configured to bias the plunger in a distal direction of the injection device, wherein the one or more recesses and/or the one or more teeth are shaped to urge the one or more teeth out of the one or more recesses when the plunger is moved in the distal direction of the injection device;

wherein an internal surface of the collar comprises one or more recesses arranged to allow the one or more toothed beams to flex outwardly when the collar is rotated, thereby releasing the plunger, wherein the one or more recesses of the collar have a first angular size greater than a second angular size of the one or more toothed beams, thereby allowing rotation of the collar with respect to the plunger and rear casing after the release of the plunger;

wherein the cam track comprises:

a first portion configured to, during retraction of the needle shroud into the injection device body, guide the shroud pin from an initial position to a hold position and cause the collar to rotate relative to the injection device body, wherein the injection device is configured to dispense medicament when the shroud pin is in the hold position;

a second portion configured to, during extension of the needle shroud from the injection device body subsequent to the retraction, guide the shroud pin from the hold position to a final position and cause the collar to further rotate relative to the injection device body in a same direction as the first portion; and a non-return surface that is radially fixed relative to the collar and configured to, subsequent to the extension, prevent further retraction of the needle shroud into the injection device body, wherein the non-return surface comprises a proximal edge and a distal edge each angled to cause the collar to (i) further rotate relative to the injection device body in the same direction as the first portion and (ii) trap the shroud pin, wherein the non-return surface comprises a first vertical edge linking an end of the second portion to the distal edge of the non-return surface, wherein the non-return surface comprises a second vertical edge linking a most distal part of the distal edge to a most proximal part of the proximal edge;

wherein the first angular size of the one or more recesses of the collar is at least large enough to allow the rotation of the collar while the one or more toothed beams are flexed outwardly into the one or more recesses of the collar, such that the shroud pin reaches the non-return surface subsequent to the release of the plunger.

2. The injection device of claim 1, wherein:

the first portion of the cam track comprises a first angled cam track edge arranged to convert at least a portion of inward axial motion of the needle shroud into rotational motion of the collar; and the second portion of the cam track comprises a second angled cam track edge arranged to convert at least a portion of outward axial motion of the needle shroud into rotational motion of the collar.

3. The injection device of claim 2, wherein the first angled cam track edge and the second angled cam track edge partially overlap in an azimuthal direction of the collar.

4. The injection device of claim 1, wherein the first portion and second portion of the collar partially overlap at least at the hold position.

5. The injection device of claim 1, wherein the injection device further comprises a control spring to bias the needle shroud towards an extended position.

6. The injection device of claim 1, wherein each tooth of the one or more teeth comprises a bevel at a proximal end of the tooth.

7. The injection device of claim 1, wherein the shroud pin extends inwardly from the needle shroud in a radial direction.

8. The injection device of claim 1, wherein the injection device further comprises a needle, and wherein the needle shroud is arranged to shroud the needle when in an extended position.

9. The injection device of claim 1, wherein the injection device further comprises a medicament cartridge containing a medicament.

10. A collar for an injection device comprising:

an internal surface comprising one or more recesses arranged to allow one or more toothed beams of a rear casing of the injection device to flex outwardly when the collar is rotated, thereby releasing a plunger of the injection device, wherein the one or more recesses of the collar have a first angular size greater than a second angular size of the one or more toothed beams, thereby allowing rotation of the collar with respect to the plunger and rear casing after the release of the plunger;

a cam track engageable with a shroud pin of a needle shroud, wherein the cam track comprises:

a first portion comprising a first angled cam track configured to, during retraction of the needle shroud into an injection device body of the injection device, convert at least a portion of inward axial motion of the needle shroud into rotational motion of the collar and guide the shroud pin from an initial position to a hold position to cause the collar to rotate relative to the injection device body, wherein the injection device is configured to dispense medicament when the shroud pin is in the hold position;

a second portion comprising a second angled cam track configured to, during extension of the needle shroud from the injection device body subsequent to the retraction, convert at least a portion of outward axial motion of the needle shroud into rotational motion of the collar and guide the shroud pin from the hold position to a final position to cause the collar to further rotate relative to the injection device body in a same direction as the first portion; and a non-return surface that is radially fixed relative to the collar and configured to, subsequent to the extension, prevent further retraction of the needle shroud into the injection device body, wherein the non-return surface comprises a proximal edge and a distal edge each angled to cause the collar to (i) further rotate relative to the injection device body in the same direction as the first portion and (ii) trap the shroud pin, wherein the non-return surface comprises a first vertical edge linking an end of the second portion to the distal edge of the non-return surface, wherein the non-return surface comprises a second vertical edge linking a most distal part of the distal edge to a most proximal part of the proximal edge;

wherein the first angular size of the one or more recesses of the collar is at least large enough to allow the rotation of the collar while the one or more toothed beams are flexed outwardly into the one or more recesses of the collar, such that the shroud pin reaches the non-return surface subsequent to the release of the plunger.

11. The collar of claim 10, wherein the first angled cam track edge and the second angled cam track edge partially overlap in an azimuthal direction of the collar.

12. The collar of claim 10, wherein the first portion and second portion of the collar partially overlap at least at the hold position.

13. The collar of claim 10, wherein an internal surface of the collar comprises one or more recesses.

14. A method for securing a needle shroud of an injection device after use, the method comprising:

biasing a plunger of the injection device in a distal direction of the injection device using a biasing force;

converting a portion of the biasing force into an outward force on one or more toothed beams of a casing using one or more recesses on the plunger;

during retraction of the needle shroud into an injection device body, guiding a shroud pin of the needle shroud from an initial position to a hold position using a first portion of a cam track of an injection device collar, the first portion of the cam track comprising a first angled cam track edge arranged to convert at least a portion of inward axial motion of the needle shroud into rotational motion of the collar, the guiding causing the injection device collar to rotate relative to the injection device body, wherein the injection device is configured to dispense medicament when the shroud pin is in the hold position;

retaining one or more teeth of the one or more toothed beams in an engaged position with the one or more recesses on the plunger during at least a portion of the retraction of the needle shroud into the injection device;

allowing the one or more toothed beams to flex outwardly at the hold position, thereby releasing the plunger, wherein an internal surface of the collar comprises one or more recesses arranged to allow the one or more toothed beams to flex outwardly when the collar is rotated, thereby releasing the plunger, wherein the one or more recesses of the collar have a first angular size greater than a second angular size of the one or more toothed beams, thereby allowing rotation of the collar with respect to the plunger and rear casing after the release of the plunger;

during extension of the needle shroud from the injection device body subsequent to the retraction, guiding the shroud pin from the hold position to a final position using a second portion of the cam track of the injection device collar, the second portion of the cam track comprising a second angled cam track edge arranged to convert at least a portion of outward axial motion of the needle shroud into rotational motion of the collar, the guiding causing the injection device collar to rotate relative to the injection device body in a same direction as the guiding of the first portion; and subsequent to the extension of the needle shroud, preventing further retraction of the needle shroud into the injection device body using a non-return surface that is radially fixed relative to the injection device collar, wherein the non-return surface comprises a proximal edge and a distal edge each angled to cause the collar to (i) further rotate relative to the injection device body in the same direction as the first portion and (ii) trap the shroud pin, wherein the non-return surface comprises a first vertical edge linking an end of the second portion to the distal edge of the non-return surface, wherein the non-return surface comprises a second vertical edge linking a most distal part of the distal edge to a most proximal part of the proximal edge wherein the first angular size of the one or more recesses of the collar is at least large enough to allow the rotation of the collar while the one or more toothed beams are flexed outwardly into the one or more recesses of the collar, such that the shroud pin reaches the non-return surface subsequent to the release of the plunger.

15. The method of claim 14, wherein the first angled cam track edge and the second angled cam track edge partially overlap in an azimuthal direction of the collar.

16. The method of claim 14, wherein the first portion and second portion of the collar partially overlap at least at the hold position.

17. The method of claim 14, wherein the non-return surface comprises an angled surface or horizontal surface arranged to trap the shroud pin when further retraction of the needle shroud into the injection device body is attempted.

18. The method of claim 14, wherein each tooth of the one or more teeth comprises a bevel at a proximal end of the tooth.

19. The method of claim 14, further comprising expelling medicament from a medicament cartridge of the injection device.

* * * * *